United States Patent [19]

Alvarez et al.

[11] Patent Number: 5,465,734
[45] Date of Patent: Nov. 14, 1995

[54] ADJUSTABLE TONGUE POSITIONING DEVICE AND METHOD

[75] Inventors: Ramiro M. Alvarez, Fremont; Susan J. Lea, Berkeley, both of Calif.

[73] Assignee: Snorex, Inc., Reno, Nev.

[21] Appl. No.: 223,332

[22] Filed: Apr. 5, 1994

Related U.S. Application Data

[63] Continuation-in-part of Ser. No. 180,262, Jan. 12, 1994, abandoned.

[51] Int. Cl.⁶ ............................................. A61F 5/56
[52] U.S. Cl. ............................................. 128/848; 128/860
[58] Field of Search ............................... 128/848, 859, 128/860, 861, 862; 433/6

[56] References Cited

U.S. PATENT DOCUMENTS

| | | | |
|---|---|---|---|
| 4,169,473 | 10/1979 | Samelson | 128/136 |
| 4,196,724 | 4/1980 | Wirt et al. | 128/860 |
| 4,304,227 | 12/1981 | Samelson | 128/848 |
| 4,593,686 | 6/1986 | Lloyd et al. | 128/136 |
| 4,676,240 | 6/1987 | Gardy | 128/207 |
| 4,867,147 | 9/1989 | Davis | 128/859 |
| 5,003,994 | 4/1991 | Cook | 128/848 |
| 5,046,512 | 9/1991 | Murchie | 128/859 |
| 5,117,816 | 6/1992 | Shapiro et al. | 128/848 |
| 5,154,184 | 10/1992 | Alvarez | 128/848 |
| 5,316,020 | 5/1994 | Truffer | 128/848 |
| 5,373,859 | 12/1994 | Forney | 128/846 |

OTHER PUBLICATIONS

Lowe, Dental Appliances for the Treatment of Snoring and OSA, Principles & Practice of Sleep Medicine, 2nd Edn. Kryer et al. Eds. pp. 722–735, 1993.

*Primary Examiner*—Robert A. Hafer
*Assistant Examiner*—Michael O'Neill

[57] ABSTRACT

An apparatus is provided for positioning a user's tongue to bring the tongue forward, to decrease obstructions in the user's airway and reduce snoring. The apparatus comprises a tongue sleeve which is configured to retain the forward extent of the user's tongue. In preferred embodiments, the tongue sleeve has narrowed inner dimensions at a point along the length of the sleeve. This narrowing acts strength the suction when the user's tongue is positioned within the sleeve. Preferably, the narrowing portions comprise an annular constricted portion. The tongue sleeve has one or more airways which may either comprise complete tubes or air channels formed in the tongue sleeve. A number of airways may be provided. In one embodiment, the airway comprises a tube configured to connect with a positive airway pressure supply means to maintain the patency of the user's upper respiratory tract. A shield means which serves to position the tongue sleeve with respect to the user's mouth is attached by attachment means to the tongue sleeve. The shield means is restrained by the user's lips. In a preferred embodiment, the attachment means is adjustable and may comprise a series of notches along the tongue sleeve which are adapted to receive the shield means. Typically, the attachment means in conjunction with the shield means moves the user's tongue forward from 1 to 4 centimeters. The shield means may also comprise a shelf which receives the user's lips or the user's lips and teeth. In some embodiments, the shelf has extensions to accommodate the user's dental arch. Preferably, an elastomeric, moldable or conformable material is attached to the shelf.

33 Claims, 12 Drawing Sheets

ADJUSTABLE TONGUE POSITIONING DEVICE AND METHOD

CROSS-REFERENCE TO RELATED APPLICATIONS

This application is a continuation-in-part of application Ser. No. 08/180,262, filed Jan. 12, 1994, and entitled Adjustable Anti-Snoring Device, that was expressly abandoned on 25 May 1995.

FIELD OF THE INVENTION

This invention relates generally to apparatus for treating snoring to minimize same. More particularly, it concerns improvements in tongue-position control and breathing enhancements in such apparatus.

BACKGROUND OF THE INVENTION

Prior devices for controlling snoring include those disclosed in U.S. Pat. Nos. 4,169,473 and 4,304,227 to Samelson; U.S. Pat. No. 4,593,686 to Lloyd et al. and U.S. Pat. No. 4,676,240 to Gardy. Certain of such devices provide for reception of the tongue in a hollow formed by a mouth-retained holder. One problem presented by such devices lies in the lack of fit of the device to the user's tongue; for example, mouth retention of the hollow device dictates the position of the tongue socket, whereby a longer tongue is not properly or comfortably accommodated. Such prior devices also are characterized by other problems and difficulties.

For example, U.S. Pat. No. 4,169,473 to Samelson discloses a device with a rigid tongue pocket molded to a tooth channel for positioning a user's tongue. This device offers benefits over earlier devices but does not allow breathing through the user's mouth. In addition, the simple design of the tongue chamber does not retain the tongue as well as the new invention. In another example, U.S. Pat. No. 4,676,240 to Gardy discloses a one-piece device with a deep tongue pocket, with internal ridges, external ridges to engage the user's teeth and integrally molded air tubes. The simple design of the tongue chamber does not retain the tongue as well as the new invention. In addition, unlike the new apparatus, this device is not adjustable.

One invention, disclosed in U.S. Pat. No. 5,154,184 to Alvarez, provides an improved anti-snoring device free from the problems and difficulties associated with prior devices. The apparatus includes 1) a tongue sleeve configured for reception and retention of the outer extent of the user's tongue, and to be retained by the user's mouth, 2) a shield shaped to be received and retained outwardly of the user's lip, and 3) an attachment mechanism or component for adjustably attaching the shield to the tongue sleeve to permit selective adjustment of the position of the shield relative to the tongue forward extent whereby the tongue may be comfortably positioned and retained in the tongue sleeve, whereby snoring is reduced as the tongue is brought forward, out of the mouth, and incremental forward movement of the shield will move the tongue further forward, with lessened airway obstruction.

Typically, the tongue sleeve has a forward position, and the attachment mechanism projects outwardly of and about the forward position, sidewardly of the tongue sleeve. The shield can extend at least partway about the tongue sleeve, with selective attachment to the latter. The shield may include upper and lower portions to fit outwardly of the user's upper and lower lips. The shield may be loosely carried by the tongue sleeve to provide breathing passages therebetween, and to allow limited tongue positioning of the tongue sleeve relative to the shield.

The attachment mechanism preferable includes notches presented sidewardly for selected engagement with the shield structure. In this regard, the notches may be carried by a forward portion of the tongue sleeve, and are spaced to align the tongue sleeve relative to the shield. The user begins by positioning the shield at first notches nearest the face; and the shield can be progressively advanced forwardly, away from the lips, until snoring reduction and tongue comfort are achieved.

The Alvarez '184 shield preferably includes air holes 70 and 71 to facilitate breathing, particularly through the user's nose. However, some people prefer to breathe through their mouths. Most people suffer some restriction on nasal breathing at certain times, particularly when suffering from congestion caused by a cold or allergies. The '184 device could be improved by providing improved air communication for mouth breathing.

SUMMARY OF THE INVENTION

The present invention provides an anti-snoring apparatus with a tongue sleeve configured for reception and retention of the outer extent of the user's tongue, some form of airway structure in the tongue sleeve, a shield structure shaped to be received and retained on the tongue sleeve and positioned just forward of the user's lip or lips, an alternate shield structure shaped to lie along one portion of the tongue sleeve to further define the airway and further shaped to be retained just forward of the user's lip, and an attachment structure for adjustably attaching the shield structure to the tongue sleeve to permit selective adjustment of the position of the tongue sleeve relative to the tongue forward extent whereby the tongue may be comfortably positioned and retained in the tongue sleeve, whereby snoring is reduced as the tongue is brought forward, out of the mouth, and incremental forward movement of the shield will move the tongue further forward, with lessened airway obstruction.

A preferred shield includes a lip rest to support the user's lips. Another preferred shield includes a bite shelf to support the user's lips and teeth. A preferred tongue sleeve includes an airway, which may be one or more channels or enclosed tubes. Another preferred aspect of the tongue sleeve is a sealable vacuum connection.

An object of this invention is to provide an anti-snoring device designed to provide easy breathing through a user's mouth.

This and other objects and advantages of the invention, as well as the details of an illustrative embodiment, will be more fully understood from the following specification and drawings.

BRIEF DESCRIPTION OF THE DRAWINGS

FIG. 8 also illustrates a detachable tether for use with this invention.

FIG. 13 also illustrates two nasal pillows which may be used in conjunction with the apparatus.

DESCRIPTION OF THE PREFERRED EMBODIMENTS

Figure 1:
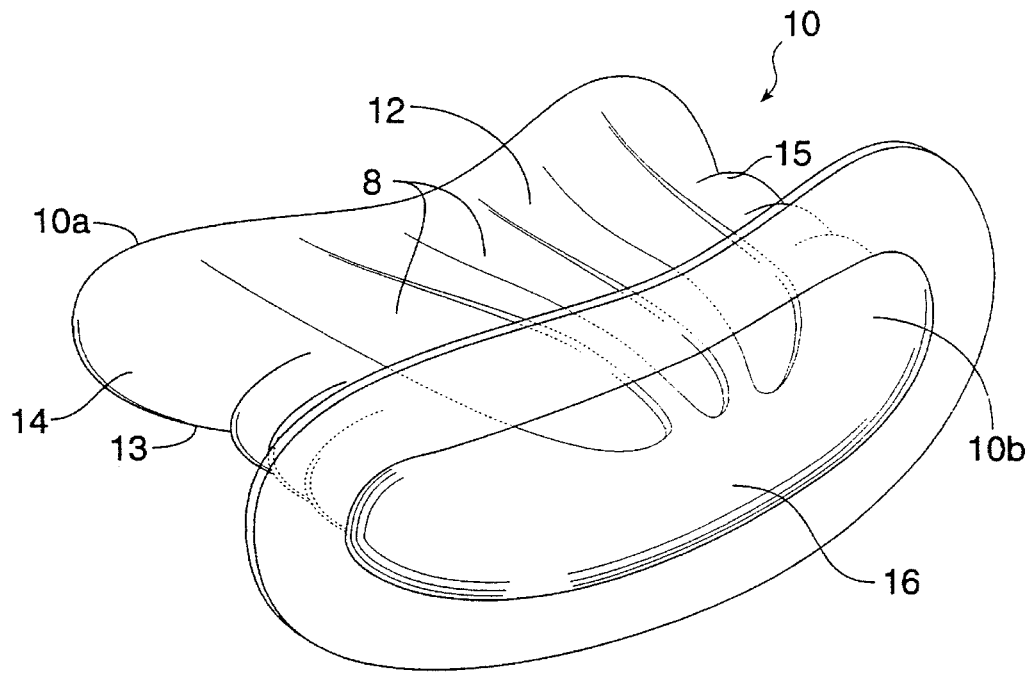
FIG. 1 illustrates a perspective view of the apparatus with a stiff shield.

In the drawings, a one-piece tongue sleeve is shaped for reception and retention of the forward extent of the user's tongue (not shown). To use the device, a user slips his or her tongue into the tongue sleeve. The tongue can be wiggled and pushed into the tongue sleeve until the tongue tip reaches the maximum forward extent of the device. If air remains in the forward portion of the device, the user can wiggle his or her tongue and allow the air to escape. In addition, the forward portion of the tongue sleeve can be gently squeezed to force air out of the forward portion. The user's tongue can relax to generally fill the forward portion of the tongue sleeve, thereby securing the user's tongue in the device. The shield device can be fitted to the tongue sleeve before or after inserting the tongue, although it is generally easier to attach the shield first.

Figure 2A:
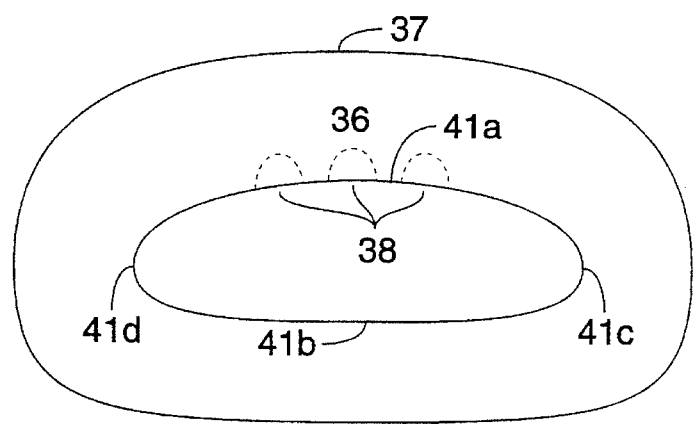
FIGS. 2A and 2B illustrate a front view taken on lines 2—2 of FIG. 3, showing the shield (2A) and tongue sleeve (2B) when disassembled.
Figure 2B:
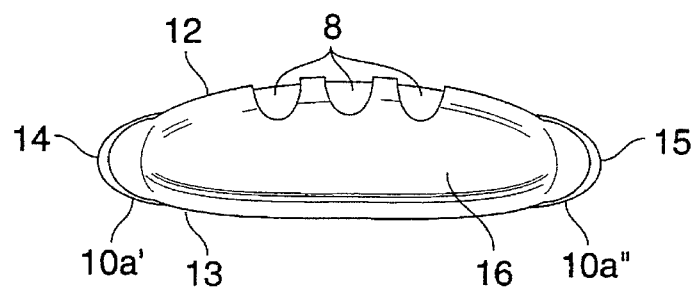
Figure 4A:
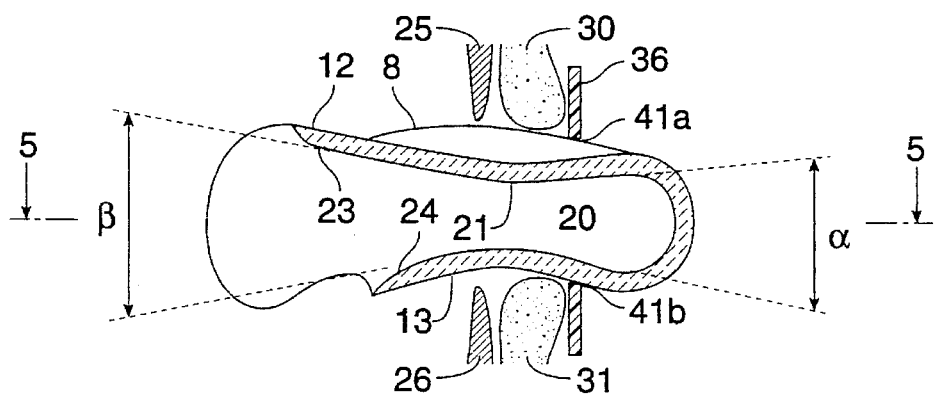
FIG. 4A illustrates a vertical section taken through the apparatus along lines 4—4 with a stiff shield when in use.
Figure 4B:
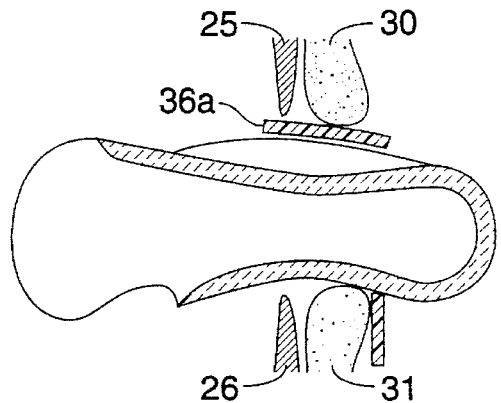
FIG. 4B illustrates a vertical section taken through the apparatus along lines 4—4 with a floppy shield when in use.
Figure 6:
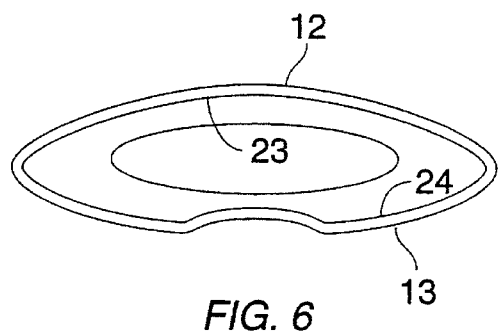
FIG. 6 illustrates a view from the rear of the tongue sleeve.

Referring to FIGS. 1 and 2B, such tongue sleeve 10 has a rearward section 10a which is "C" or crescent-shaped along the bottom wall 13 and generally flat along top wall 12. The tongue sleeve has a pocket-shaped forward section 10b integral with 10a. The forward section has upper and lower generally parallel walls 12 and 13, opposite side walls 14 and 15, which are outwardly convex, and a front wall 16, which is forwardly convex and merging with 12 and 13, and with 14 and 15. Referring to FIGS. 4A, 4B and 6, forward section 10b is sized to project forwardly of the user's lips with the tongue resting comfortably, substantially filling the cavity or compartment 20 defined by walls 12–16.

Upper and lower walls 12 and 13 flare forwardly at a small angle $\alpha$ (see FIGS. 4A, 4B) from a narrowed region 21 at the proximate joiner of sections 10a and 10b. Similarly, right and left walls 14 and 15 flare forwardly at a small angle $\alpha'$ from a narrowed region 22 at the proximate joiner of sections 10a and 10b. Region 21 and region 22 may be at approximately the same anterior position between the front and back of the apparatus, forming an annular constriction, but can be at different anterior positions. These regions together define a sort of hourglass shape, which provides a mild constriction around the tongue. The tongue forward of this restriction tends to expand slightly and fill substantially all of compartment 20. This provides mechanical retention of the tongue in addition to the simple vacuum effect relied on by prior art devices with generally straight interior chambers. In addition, since the apparatus is often made of elastomeric material, if the user clenches down on the apparatus, however lightly, this will tend to deform the apparatus and further narrow the constriction, providing additional mechanical retention. The restriction preferably is positioned so the anterior third of the tongue can expand anterior to the restriction.

Angle $\alpha$ may range from generally widening, up to about 50°, to flat or even somewhat negative (narrowing) such as about $-10°$, and preferably is between about 2° and 10°. Angle $\alpha'$, like angle $\alpha$, may range from generally widening, up to about 50°, to flat or even somewhat negative (narrowing) such as about $-10°$, and preferably is between about 2° and 10°. Angle $\alpha'$ and angle $\alpha$ are independent and so may be similar or different.

The rearward section 10a has interior upper wall 23 and interior lower crescent wall 24 that flare apart rearwardly at an angle $\beta$ and interior left wall 27 and interior right wall 28 flare apart, rearwardly, at an angle $\beta'$ to accommodate the user's tongue and fit the user's mouth. Angle $\beta$ preferably is greater than angle $\alpha$ and angle $\beta'$ preferably is greater than angle $\alpha'$ and each of these angles are independent. Each of angles $\beta$ and $\beta'$ may vary between about 0° and 60° but preferably is between about 15° and 35°.

Figure 5:
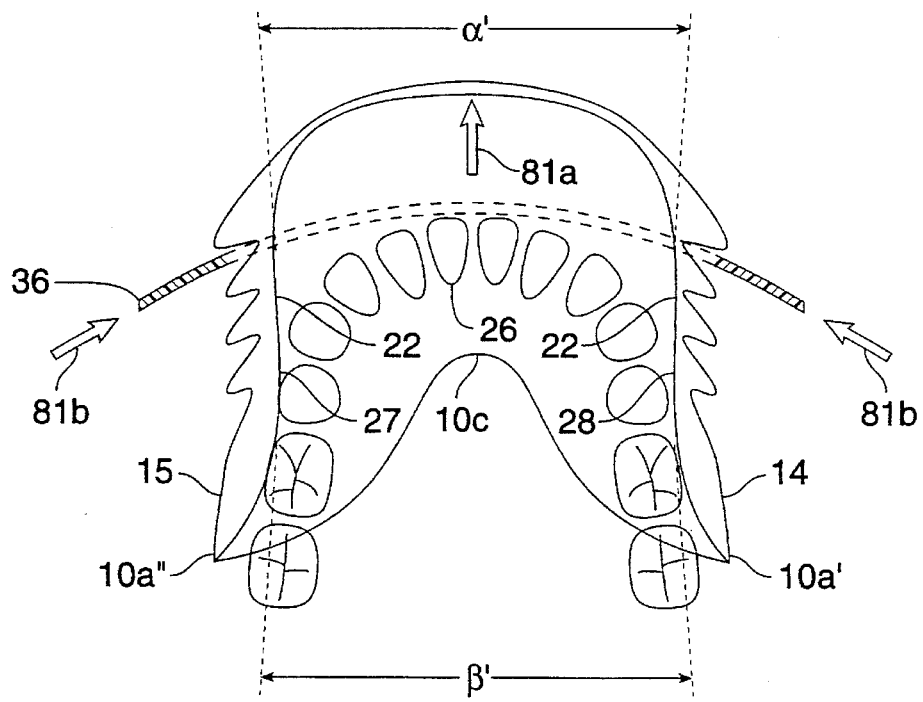
FIG. 5 illustrates a sagittal section taken through the apparatus.

The lower portion of rearward section 10a has laterally extending and rearwardly diverging subsections or lobes 10a' and 10a" which are adapted to fit the rearward curvature of a user's left and right lower teeth regions. Concave extent 10c provides relief for the lingual frenulum and the floor of the mouth of the user. This relief is particular important for users with certain mouth geometries. Referring to FIG. 5, some portion of the user's teeth rest on the top and bottom of the apparatus, keeping it away from the floor or roof of the user's mouth.

One or more channels 8 are provided in upper portion 12. Each channel preferably begins in a region near the front of the apparatus which will be in front of the user's lips and extends backwards to a region which will be behind the user's teeth. Each channel 8 provides an air passage to facilitate breathing through the user's mouth. In a preferred embodiment, three channels 8 are provided, positioned so a typical user's teeth will engage the apparatus to rest on upper surface 12 and to not occlude any channel 8. Alternatively, one or more channels may be designed into the bottom or one or both sides of the new apparatus.

Even without channels 8 a user's mouth often will allow some air to enter, for example at the side where the lips come together with the apparatus. However, it is important in many situations to have dependable air channels for easy mouth breathing. In various medical conditions, an airway can be guaranteed by inserting an endotracheal tube. This is sometimes described as airway patency. A single tube with 7 $mm^2$ internal cross section is accepted as a minimum for a normal adult. In the present apparatus, the cumulative cross section of channels 8 preferably is in excess of this value. In one preferred embodiment, each of three channels has a minimum cross section of 4.2 $mm^2$ and a maximum cross section of 4.5 $mm^2$ for a total of 12.6–13.5 $mm^2$. The channel cross section for children and infants can be adjusted according to teachings in the art.

Figure 9A:
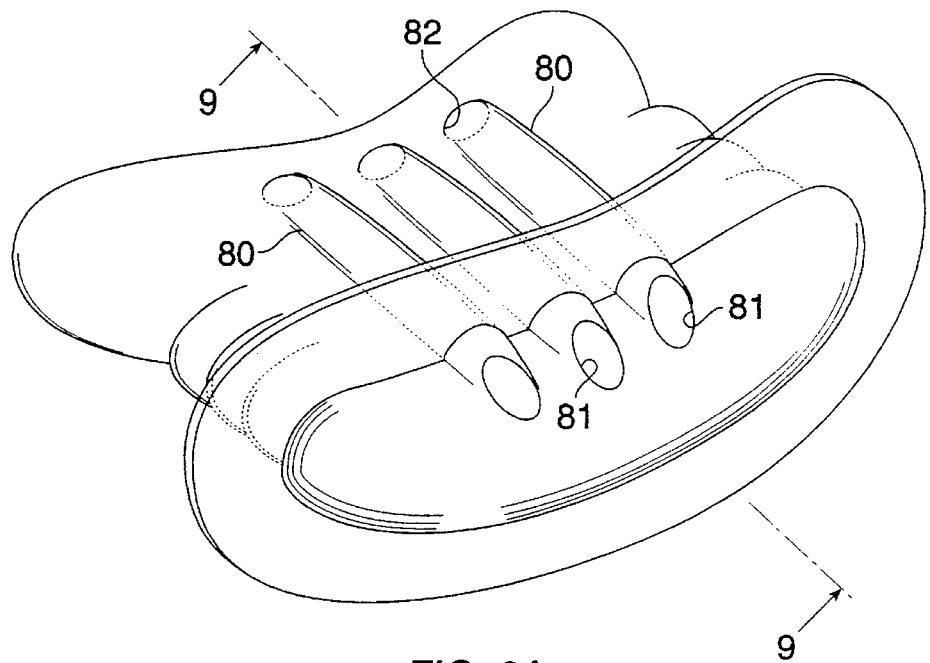
FIG. 9A illustrates a perspective view from the top front of an embodiment of the apparatus with three included tubes.
Figure 9B:
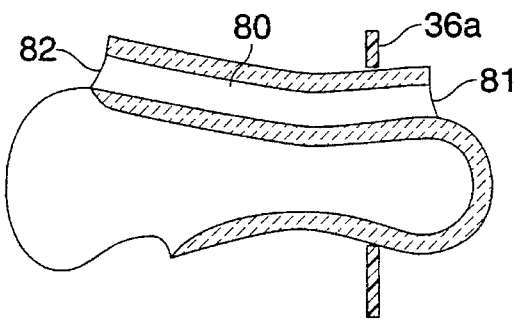
FIG. 9B illustrates a vertical section taken through the apparatus along lines 9—9.
Figure 11:
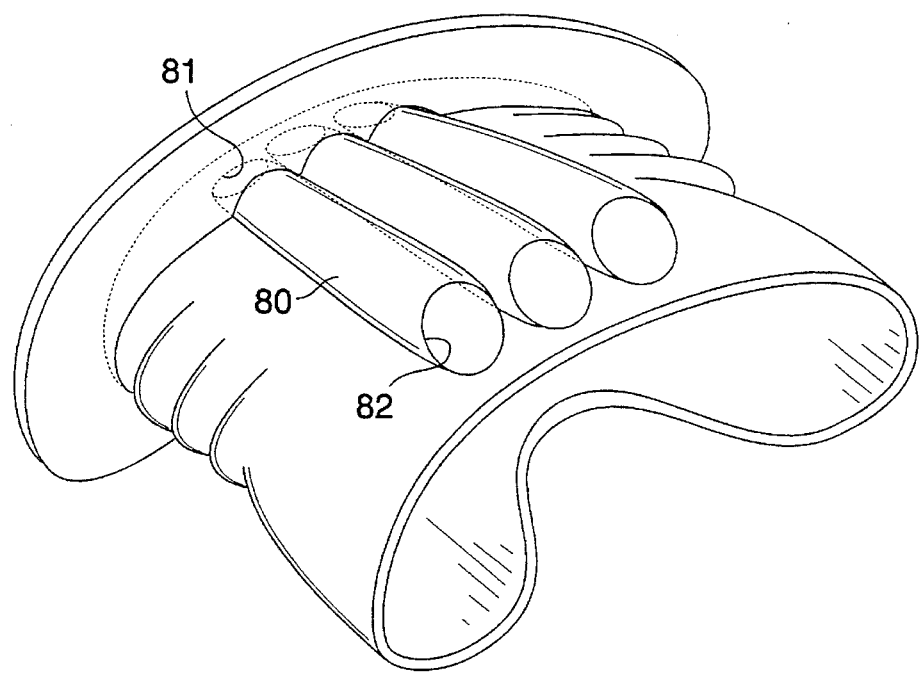
FIG. 11 illustrates a perspective view from the top rear of another embodiment of the apparatus with three included tubes.
Figure 12A:
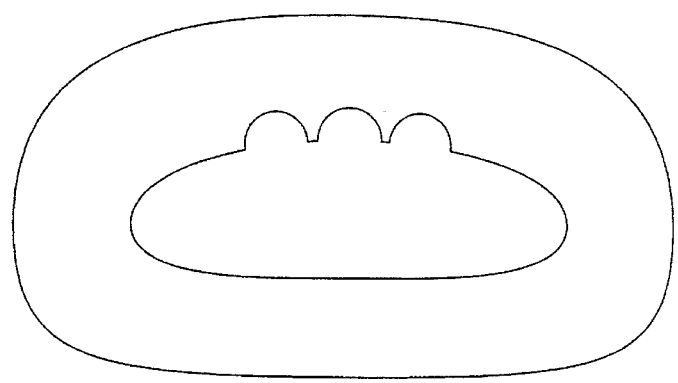
FIGS. 12A and 12B illustrate a front view of the embodiment illustrated in FIG. 11, similar to the views in FIGS. 2A and 2B, showing the shield (12A) and tongue sleeve (12B) when disassembled.
Figure 12B:
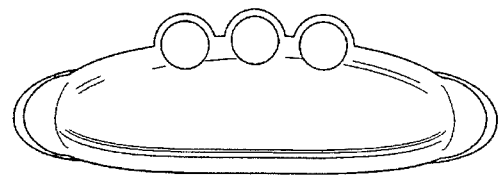
Figure 13:
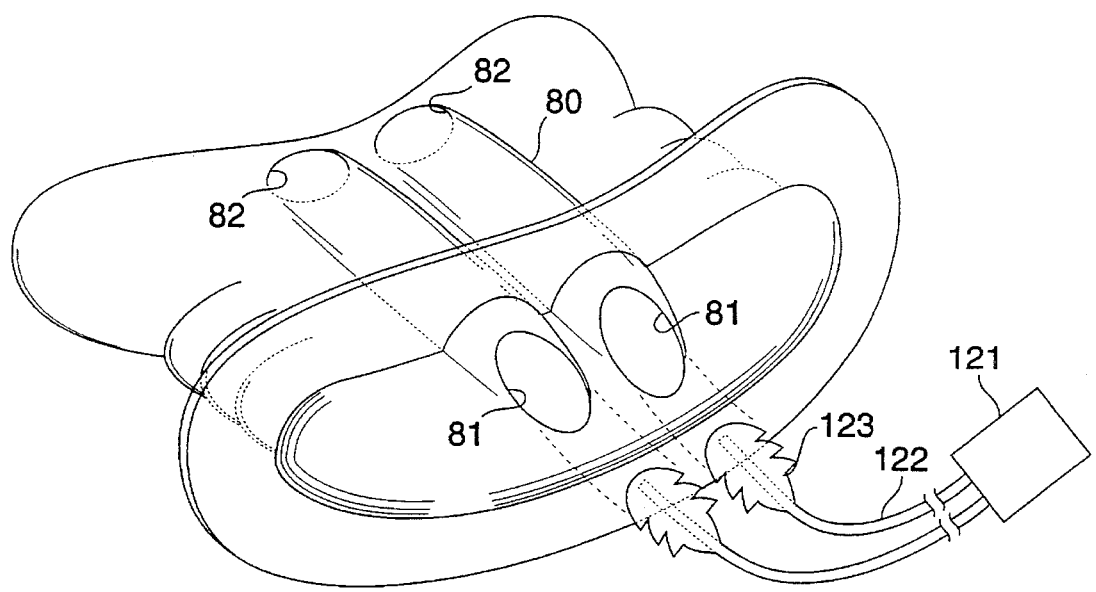
FIG. 13 illustrates a perspective view from the top front of another embodiment of the apparatus with two included robes.

Referring to FIGS. 9A and 9B, one preferred embodiment includes one or more tubes 80 which may be attached to or integrated into tongue sleeve 10. Each of tubes 80 has an opening 81 outside the user's mouth and an opening 82 inside the user's mouth. FIG. 11 illustrates an alternate embodiment with three, larger diameter tubes 80. FIG. 13 illustrates an alternate embodiment with two, still larger diameter tubes 80.

In use, the user will tend to push the device upwards towards the top of his or her mouth. Opening 82 preferably is not bevelled at an angle which might align with the roof of the user's mouth. If such a bevel were present, opening 82 could align with the soft or hard palate and close off tube 80. One useful angle for opening is approximately perpendicular to upper surface 12 of tongue sleeve 10.

The apparatus may be constructed of a variety of materials well known in the medical and dental fields. A preferred composition is molded silicone, preferably of medical grade. Other useful materials include latex, polystyrene, vinyl acetate, polyethylene and polypropylene. Elastomeric materials are preferred. A material with a durometer between about 5 to 50 is generally useful, most preferably with a durometer of about 20–30. It is possible to use a hard, non-pliable material to make the present device, but the materials already described are preferred.

The thickness of the material can be varied depending on the specific material used, but the thickness should be sufficient to allows the apparatus to be fairly rigid, but somewhat pliable. The material should not be so thin so as to make the apparatus difficult to manufacture or so thick that the apparatus forces the user's mouth open unnecessarily. For silicone, a thickness of about 0.5 to 7 millimeters, preferably 0.5 to 4 mm and more particularly about 2 to 3 mm is particularly useful.

In one preferred embodiment, the user places his or her tongue in the tongue sleeve and positions the tongue sleeve so narrowed region 21 is close to the user's incisors. The user's other teeth then rest on portion 10a of the apparatus. Since the apparatus is tapered towards narrowed regions 21 and 22, any teeth resting on the rearward portions of the apparatus will tend to push the apparatus forward. This then moves the tongue forward and achieves the desired effect.

The device is particularly beneficial because the user is not placed in an unnatural or uncomfortable position. In general, the apparatus moves the tongue forward about 1 to 4 centimeters, which is sufficient to prevent snoring in most people. This is well within the normal range of tongue extension, roughly comparable to licking ones lips. The user will sleep with his or her mouth open slightly, but this is also within the normal range of motion for typical user. With the apparatus naturally positioned, the user will press lightly on their own tongue, through 5–6 mm of elastomeric material. This amount of mouth opening is less than is encountered in normal speaking of an open vowel such as "ah." Thus the apparatus can be worn without discomfort.

In accordance with a further aspect of the invention, a shield or other retention element is provided, shaped to be retained outwardly of the user's lower lip. As illustrated in FIG. 2A, the shield preferably has the form of a shield 36 of outer edge outline 37 with inner edge outline 41 designed to accommodate tongue sleeve 10. The tongue sleeve and shield are separate parts to be relatively adjustable for mouth and tongue comfort, and preferably are similar in thickness. The shield preferably is made of a sterilizible, hard material, such as plastic. One preferred material is polycarbonate. One preferred method of sterilization is cold sterilization, widely available in dental and medical offices. The shield can also be cleaned with isopropyl alcohol.

The shield defines a generally oval shaped opening to receive and fit over the forward section 10b of the tongue sleeve, in an adjustable manner, and may engage the user's upper and lower lips. Note inner edge 41 of that opening, having elongated upper and lower portions 41a and 41b concave and adapted to fit along 12 and 13 respectively (see FIGS. 3, 4A and 4B). Left portion 41c and right portion 41d are curved and adapted to fit notches described below. In one alternate embodiment, portions 41c and 41d include a generally straight portion. FIGS. 9B and 15B illustrate alternate embodiments of shield 36 positioned on various preferred forms of tongue sleeve 10.

Figure 2C:
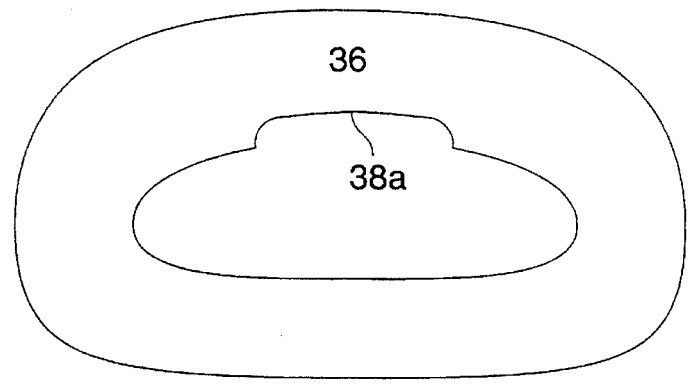
FIG. 2C illustrates an alternate form of the shield.
Figure 10A:
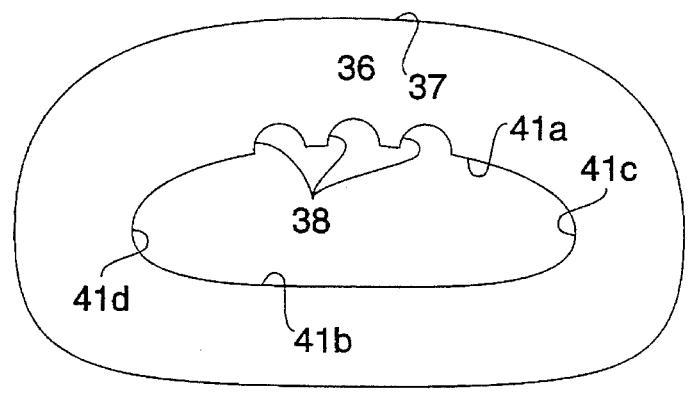
FIGS. 10A and 10B illustrate a front view of the embodiment illustrated in FIG. 9A, similar to the views in FIGS. 2A and 2B, showing the shield (10A) and tongue sleeve (10B) when disassembled.
Figure 10B:
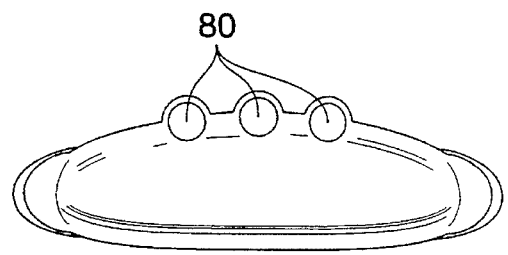

Air channels 8 allow mouth breathing while the apparatus is being worn. In one embodiment of the apparatus, notches 38 are provided to generally align with channels 8 to provide even greater air flow. Notches 38 should not be so deep as to compromise the mechanical integrity of the shield 38. Notches 38 preferably are not deeper than the smaller of 5 millimeters and half the width of shield 36. Still more preferably notches 38 are not deeper than the smaller of 3 millimeters or one third the width of shield 36. FIGS. 10A and 10B illustrate a preferred embodiment of shield 36 for tongue sleeve 10 including tubes 80. FIGS. 12A, 12B, 14A and 14B illustrate alternative forms of shield 36 and tongue sleeve 10. Referring to FIG. 2C, a single large notch 38A may be provided, spanning one or more channels, with a notch depth of 3–5 millimeters or more.

Figure 3:
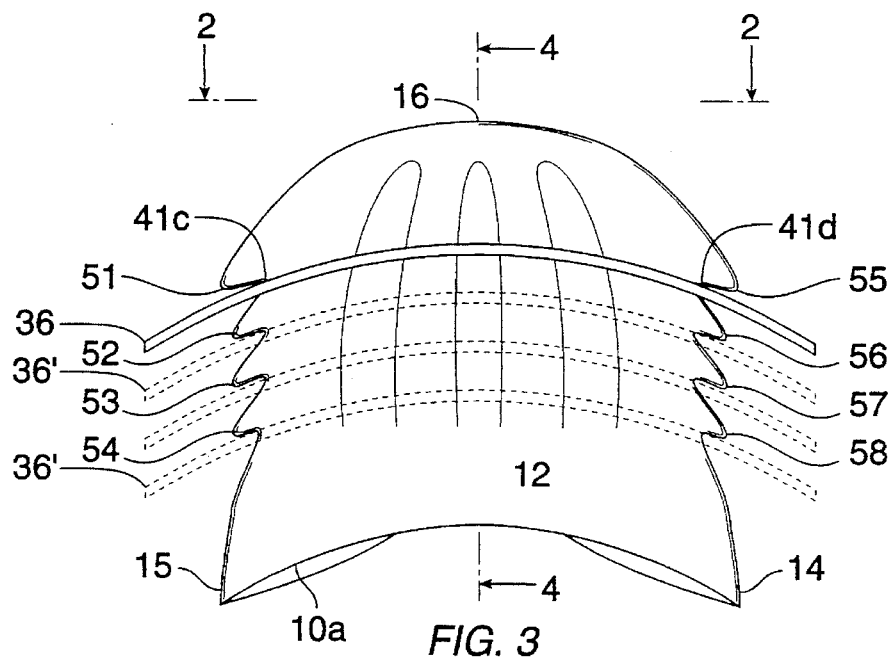
FIG. 3 is a top plan view of the apparatus incorporating the invention.

An attachment mechanism is provided for adjustably attaching the shield to the tongue sleeve, to permit selective adjustment of the position of the tongue sleeve relative to the tongue forward extent whereby the tongue may be comfortably positioned and retained in the tongue sleeve. Such attachment mechanism may advantageously take the form of notches presented sidewardly of the tongue sleeve. Referring to FIG. 3, forwardly and rearwardly spaced ridges 51, 52, 53 and 54 which define a series of notches at side 14 of 10b, and forwardly and rearwardly spaced ridges 55, 56, 57 and 58 which define a series of notches at side 15 of 10b. Ridges 51 and 55 preferably are some amount taller or longer than the others in order to provide a greater resistance to removing the shield from the last notch, which would remove it entirely from the apparatus.

The shield edge 41c is seen adjusted rearwardly to fit the notches between 51 and 52 in FIG. 3, and edge 41d fitting the notch between 55 and 56. If desired, the flexible shield can be adjusted rearwardly (see broken lines 36') so that its edge 41c fits the notch between 52 and 53, and edge 41d between 56 and 57 as well as additional positions further rearward. Thus, comfortable retention of the wearer's tongue, as during sleep, is facilitated while breathing through a channel 8 remains possible. In this regard, the shield is retained in position on the tongue sleeve which is retained in position by the mouth, and the tongue is positioned comfortably in and by the tongue sleeve, which may be adjusted relative to the shield, as desired. The user's lips are free to flex and are not outwardly constrained or overlain by the apparatus.

The shield is preferably curved to conform to the shape of a human face. The notches preferably are shaped to curved to accept the curve of the shield. This curve improves the effectiveness of the notches as well. Referring to FIG. 5, if the user pulls back on the apparatus, for example by trying to remove the tongue, the lips press shield 36 forward with force 81a. This in turn applies forces 81b to urge interior shield portions 41c and 41d into close proximity to the notches.

Figure 7:
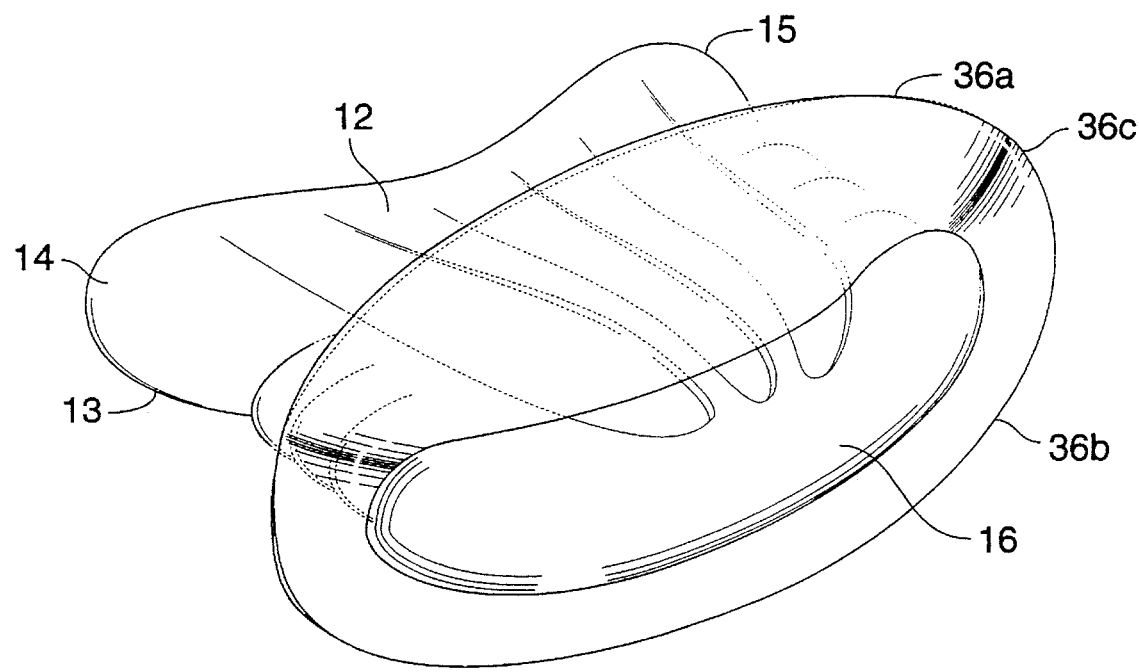
FIG. 7 illustrates a perspective view of the apparatus with a floppy shield.
Figure 8:
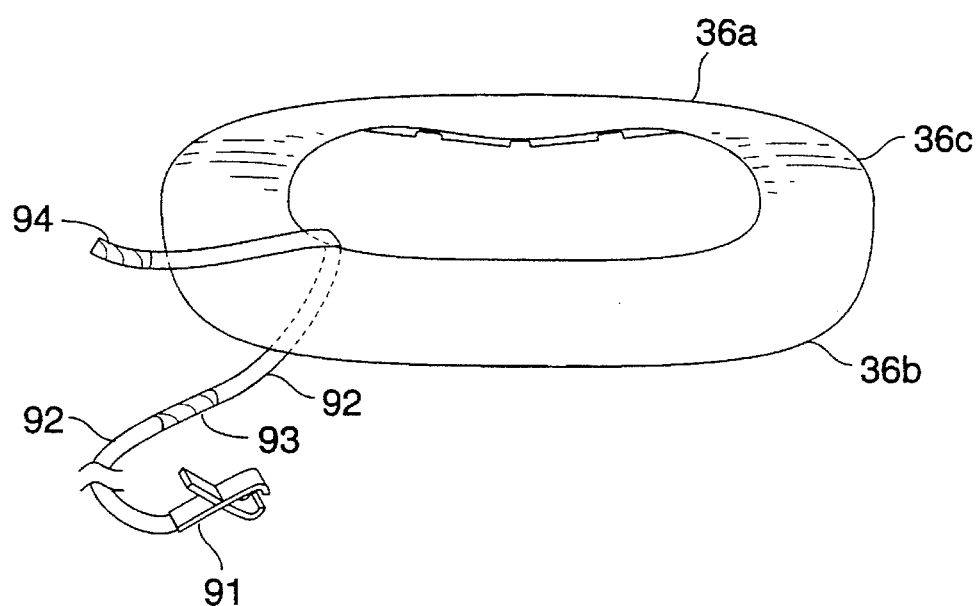
FIG. 8 illustrates a front view similar to FIG. 2A showing a floppy shield when disassembled.

In an alternate preferred embodiment, illustrated in FIGS. 7 and 8, the shield is designed to provide a floppy shield which incorporates some generally soft material so the uppermost portion 36a and lowermost portion 36b of shield 36 can fold at a hinge region 36c. This allows uppermost portion 36a to lie generally parallel to top portion 12 of the tongue sleeve. This closes each channel 8 to define a complete channel with easy communication between the inside of a user's mouth and the outside. The user's lower lip will be behind lowermost shield portion 36b and the user's upper lip should be in a generally parallel position along the top of the apparatus. Upper portion 41a of the inside edge of shield 6 should extend past the user's top lip to keep at least one channel 8 open to the outside air.

Once the user's tongue is in the tongue sleeve and the shield is in place, the user's lower lip presses lightly against the shield, compressing the lip slightly. When using the upright shield 36, the user's upper lip will be slightly compressed as well.

Figure 15A:
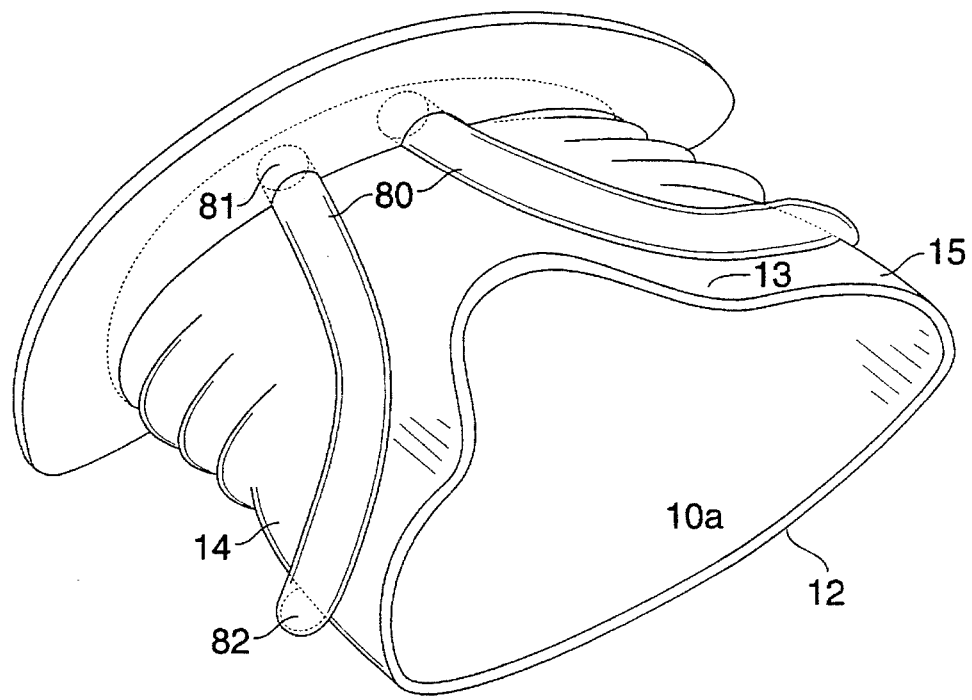
FIG. 15A illustrates a perspective view from the rear bottom of another embodiment of the apparatus with two included tubes on the bottom of the tongue sleeve.
Figure 15B:
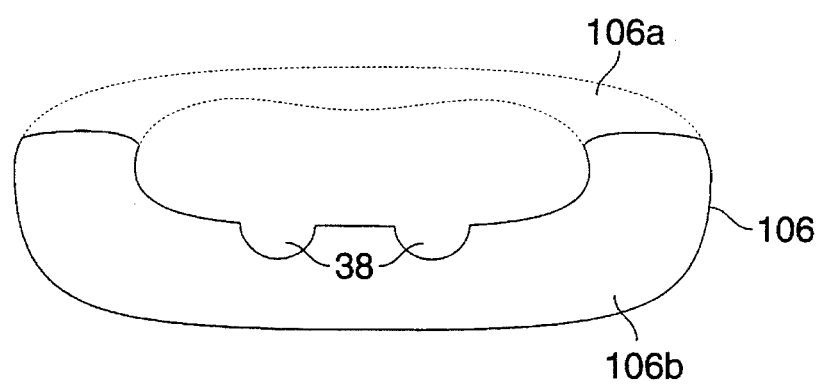
FIGS. 15B and 15C illustrate a front view of the embodiment illustrated in FIG. 15A, similar to the views in FIGS. 2A and 2B, showing the shield (15B) and tongue sleeve (15C) when disassembled.
Figure 15C:
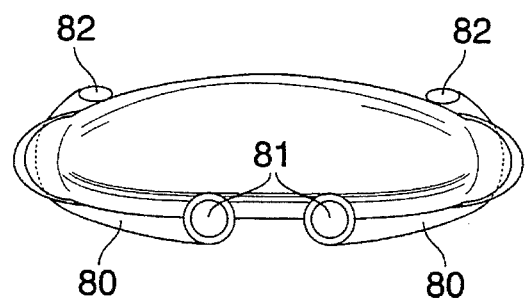

Referring to FIGS. 15A, 15B and 15C, another preferred form of the apparatus includes one or more tubes 80 on the bottom of tongue sleeve 10 which curve around tongue sleeve to connect outside air at inlet 81 to outlet 82 inside the user's mouth. This is particularly useful in conjunction with shield 106 which has lower portion 106b but has little (dotted line) or no upper portion 106a.

Figure 16A:
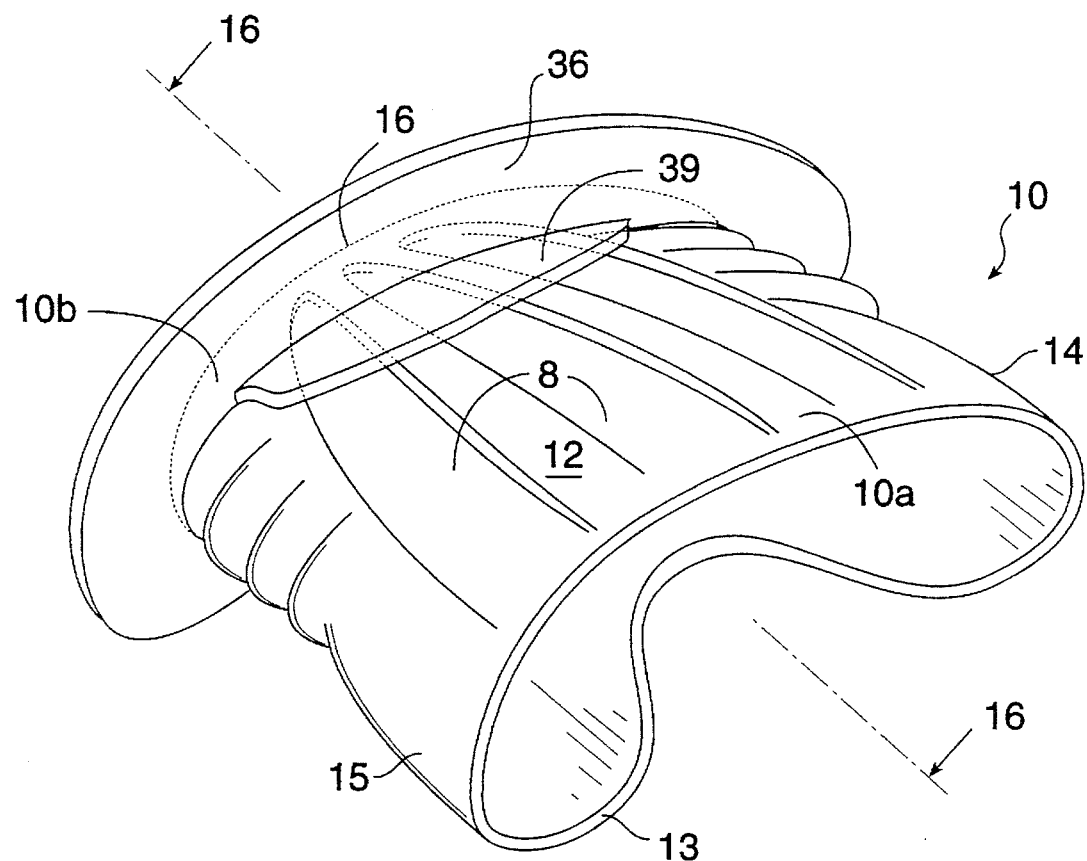
FIG. 16A illustrates a perspective view from the top rear of the apparatus showing the lip-rest shield.
Figure 16B:
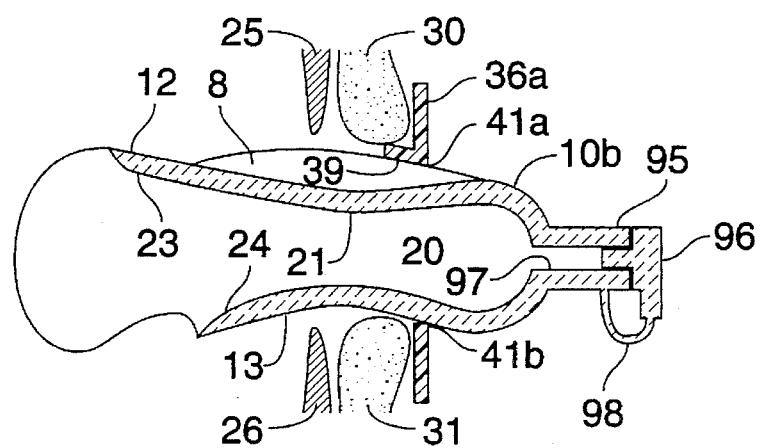
FIG. 16B illustrates a cross-sectional view taken on lines 16—16 of FIG. 16A, showing the shield when disassembled.

In accordance with yet a further aspect of the invention, a vacuum fitting can be provided to facilitate drawing air from within the forward section of the tongue sleeve. Referring to FIG. 16B, forward section 10b of tongue sleeve 10 can be fitted with vacuum fitting 95 connecting with compartment 20 in forward section 10b. Vacuum fitting 95 can be reversibly sealed by a variety of apparatuses and methods known in the art. FIG. 16B illustrates plug 96 secured by integral tether 98 and fitted inside vacuum channel 97 to seal vacuum fitting 95. Alternative valve devices include a slidable valve, a one way valve, a normally closed ball valve and other valves known in the art.

The basic device, without the vacuum fitting, can be secured readily by a conscious user. In typical use, the user will position the shield on the tongue sleeve, then insert his or her tongue into the tongue sleeve. The forward portion of the tongue sleeve can be gently squeezed, as needed, to expel entrapped air.

However, if the user is unconscious, uncommunicative, or uncooperative it may be more difficult to position the device. This is particularly true for anesthetized individuals or infants. Adding the vacuum fitting allows the user or a second person to connect the fitting to a source of vacuum, roughly position the user's tongue, apply a vacuum to pull the tongue into the tongue sleeve, and then close off the vacuum fitting. The valve fitting should be easily sealable so as to maintain the user's tongue in position in the tongue sleeve. Suitable sources of vacuum include a variety of suction devices found in many medical environments, as well as a detachable tube to which a person can apply vacuum by sucking. In some applications, a second person may simply position his or her mouth directly on the vacuum fitting and apply negative pressure.

The vacuum fitting is particularly useful in certain applications. If a second person notices that the user's tongue is slipping out of the tongue sleeve, the second person can apply vacuum to reposition the tongue. For an infant, particularly one at risk of sudden infant death syndrome, a parent or other person can place the tongue sleeve over an infant's tongue, then gently apply negative pressure to position the infant's tongue in the tongue sleeve.

A variety of other shield may be useful in practicing the present invention. Referring to FIGS. 16A and 16B, one preferred shield includes lip rest 39, extending rearward from upper portion 36a of shields 36 at approximately a right angle. Lip rest 39 preferably extends about 7 to 10 millimeters from shield 36. This forms a small landing area for the user's upper lip 30 to rest on the shield. The user's upper teeth 25 rest on upper surface 12 of tongue sleeve 10.

The main opening in shield 36 can be designed to just fit tongue sleeve 10 but in one preferred embodiment, an additional space of 0.5 to two millimeters between the upper surface 12 of tongue sleeve 10 and upper inner edge 41a can be provided.

Figure 16C:
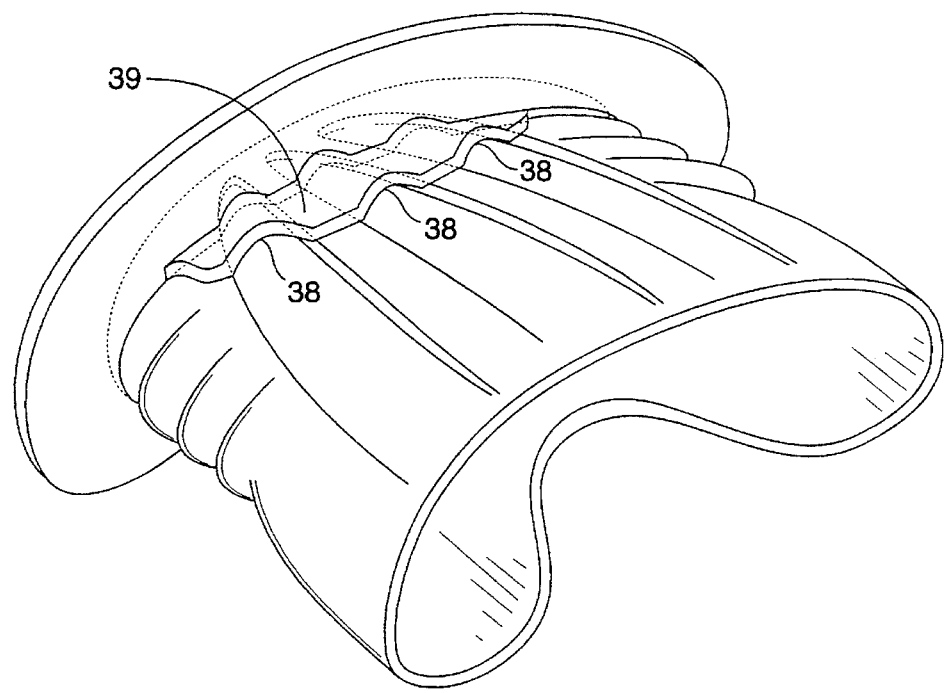
FIG. 16C illustrates a perspective view of a preferred embodiment of an apparatus with air channels.

In one preferred embodiment, lip rest 39 is angled to be generally parallel with top surface 12 of tongue sleeve 10 at one or more attached positions of shield 36. Angle ∠39–36 thus may be somewhat less than 90°, preferably between about 70 and 90°. In another preferred embodiment (not shown), angle ∠39–36 is approximately 90°, which, when upper surface 12 is angled relative to shield 36, leaves a significant gap between upper inner edge 41a and upper surface 12 of tongue sleeve 10. In the preferred embodiment illustrated in FIG. 16C, the shield of FIG. 16A can be modified to include "scallop" notches 38' in lip rest 39 corresponding to one or more air channels 8 to allow improved air flow when the device is used. Some of the dimensions of notches 38' may be like those of notches 38 described above with regard to FIG. 2B.

Figure 17A:
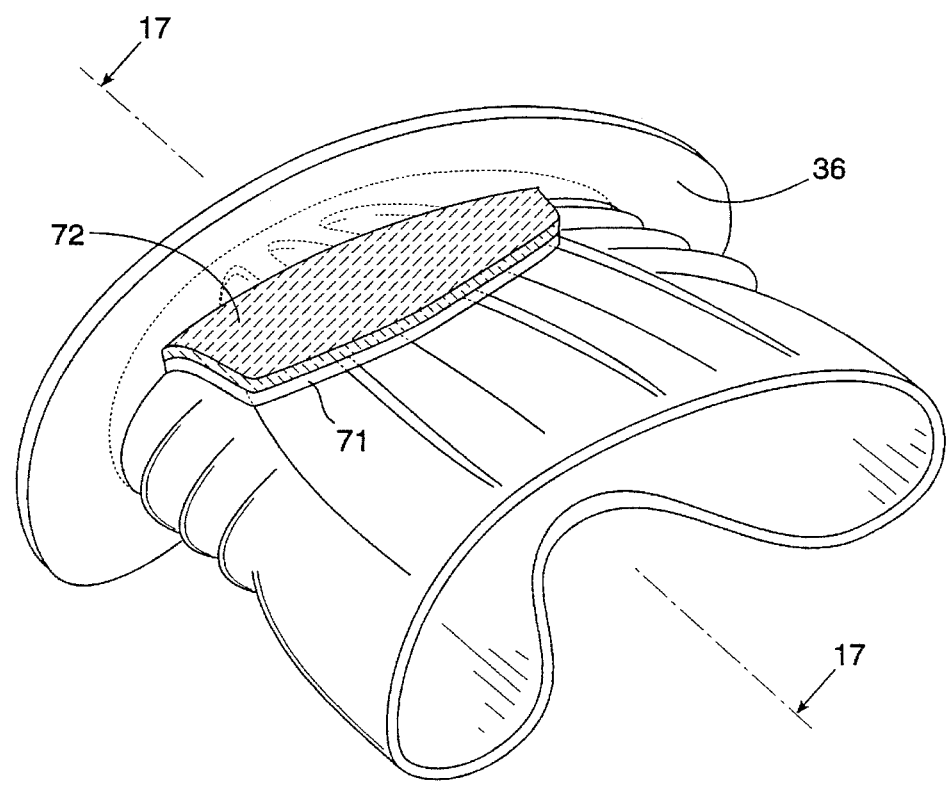
FIG. 17A illustrates a perspective view from the top rear of the apparatus showing the lip-shelf shield.
Figure 17B:
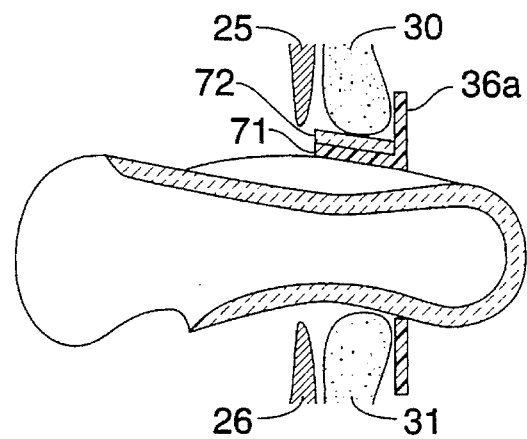
FIG. 17B illustrates a vertical section taken through the apparatus along lines 17—17 with the lip-shelf shield when in use.
Figure 18A:
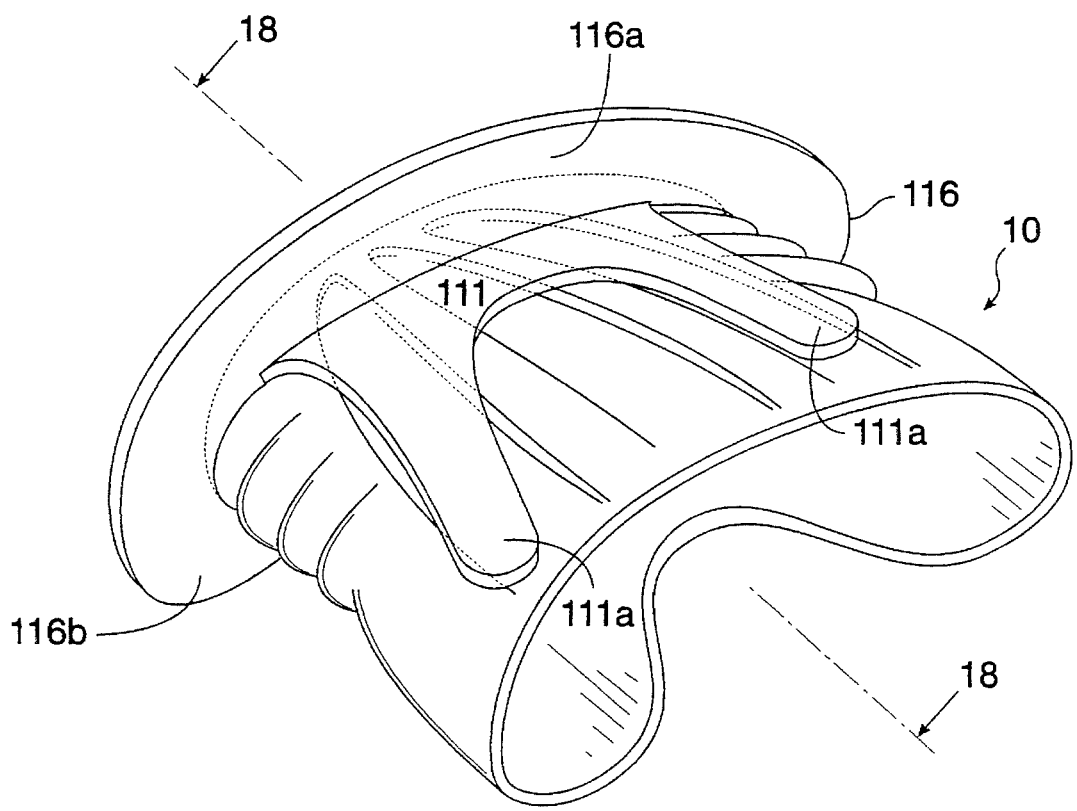
FIG. 18A illustrates a perspective view from the top rear of the apparatus showing an alternate embodiment of the shield, with a lip-shelf.
Figure 18B:
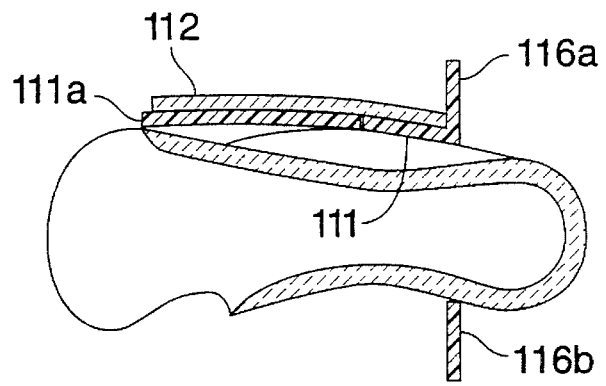
FIGS. 18B, 18C and 18D illustrate a vertical section taken through the apparatus along lines 18—18 with different embodiments of the lip-shelf shield when in use.
Figure 18C:
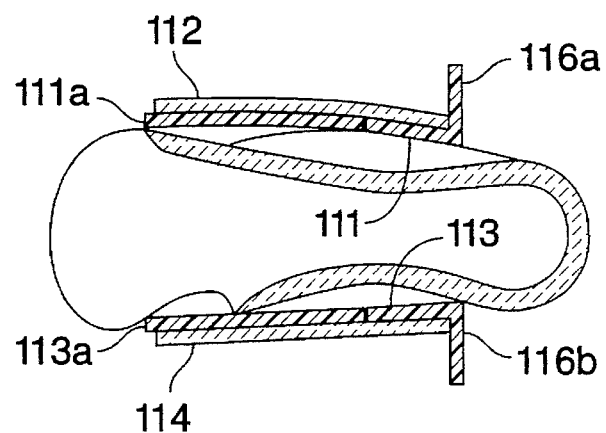
Figure 18D:
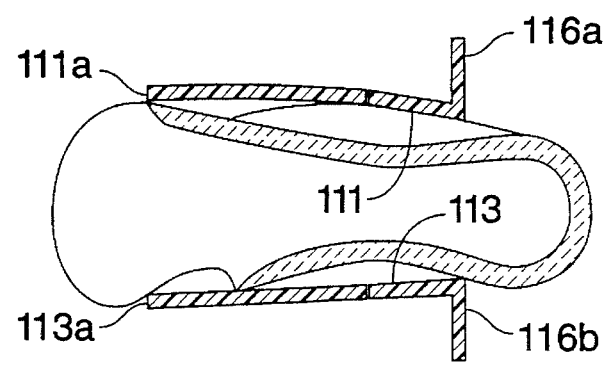

Referring to FIGS. 17A and 17B, one preferred embodiment includes shield 36 incorporating bite shelf 71 extending rearward from upper portion 36a of shield 36. Bite shelf 71 preferably extends 8 to 20 millimeters from shield 36. The user's upper lip 30 and teeth 25 rest on or above bite shelf 71. The angle of connection may be similar to that discussed above for lip shelf 39. Scallop notches 38' such as those shown in FIG. 16C can be incorporated into bite shelf 71. A person's teeth should not rest on a hard surface for an extended period of time. A period of even several hours should generally be acceptable, but wearing an apparatus repeatedly may be detrimental to a user's teeth, jaw or dentition. If bite shelf 71 is made of a hard material, bite shelf 71 may be covered partially or completely with pad 72, where pad 72 is made of a relatively soft material, preferably an elastomeric material such as silicone. A user's teeth can then rest on pad 72 but be maintained in position by underlying bite shelf 71. Each channel 8 is kept open by shield 71.

Referring to FIGS. 18A, 18B, 18C and 18D, another preferred embodiment including a bite shelf includes bite shelf 111 extending rearward from upper portion 116a of shield 116, above apparatus 10. Bite shelf 111 includes rear shelf portions 111a, configured to conform generally to the shape of a user's upper dental arch. An alternative embodiment includes lower bite shelf 113 extending rearward from lower portion 116b of shield 116, with rear shelf portions 113a configured to conform generally to the shape of the user's lower dental arch. Bite shelves 111 and 113 can be used together in the same device, or a device may include only one of the bite shelves.

It is generally easier to manufacture a bite shelf of the same material as shield 116, which, as discussed above for shield 36, preferably is a hard material. However, as discussed above, long term biting on a hard material can lead to dental complications. In one implementation, illustrated in FIG. 18D, each of bite shelves 111 and 113, if present, are made of a pliable or elastomeric material such as silicone. In a preferred implementation, illustrated in FIG. 18C, bite shelf 111, if present, is covered with elastomeric material 112 and bite shelf 113, if present, is covered with elastomeric material 114. In an alternate embodiment either or both of materials 112 and 114 are configurable material which can be molded to adapt to a specific user's dental arches. In one preferred embodiment, this material is a bondable material, such as one of many routinely used by dentists. The material could be a putty, a thermosetting plastic, or other suitable material. One preferred material is a dental acrylic, such as a cold cure orthodontic resin. The L.D. Caulk Division of DenstPly, International, of Milford, Del. 19963-0359, makes a variety of suitable two-part resins. One useful material is catalog number 651003. Such a moldable material can be bonded to either or both of bite shelves 111 and 113 and customized to a patient's teeth. If both upper and lower bite shelves are used, the molding process can be used to position the patient's jaws in a desired position. One currently used treatment for snoring is to position the lower jaw somewhat forward of the upper jaw. This can be easily achieved using the molding materials and shield of this invention. Almost every dentist is familiar with the use of such molding materials.

The basic invention can be used in other useful ways. One particular useful embodiment is designed for use with nasal CPAP or continuous positive airway pressure (CPAP) procedures. In treating various medical conditions, including sleep apnea, CPAP treatment is prescribed. Conventional machines are available in various forms to deliver pressurized air to a patient. In one form, a mask is fitted to cover the user's nose and mouth. In another form, two tubes are fitted with soft, ribbed ends to detachable engage a user's nostrils. This form is sometimes referred to as "nasal pillows." The conventional CPAP machines, however, suffer from a number of shortcomings and contraindications which are well known in the art. These include encephalitis, drying of the eye socket, rhinitis, and general discomfort when using the machine.

Figure 14A:
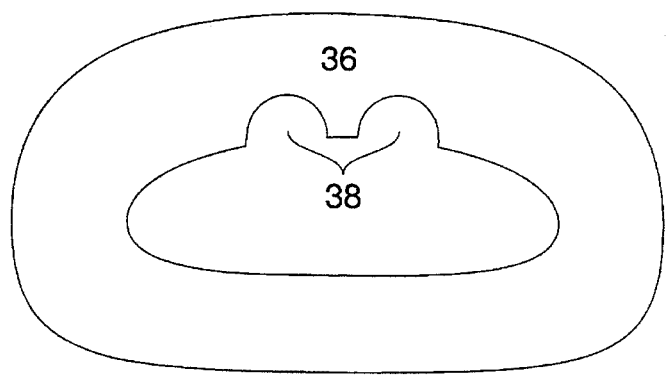
FIGS. 14A and 14B illustrate a front view of the embodiment illustrated in FIG. 13, similar to the views in FIGS. 2A and 2B, showing the shield (14A) and tongue sleeve (14B) when disassembled.
Figure 14B:
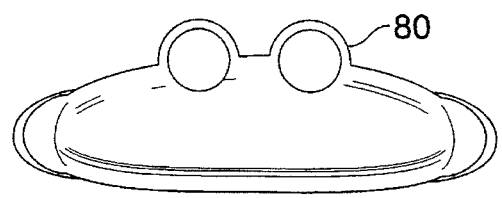

Referring to FIG. 13, tongue sleeve 10 is fitted with two tubes 80, each with an inlet 81 at the front of the apparatus, outside the user's mouth, and outlet 82 at the rear of the apparatus, inside the user's mouth. Each of tubes 80 is sized to approximate a normal human nostril so that each of nasal pillows 123 can securely but removably engage an inlet 81. Each of pillows 123 is connected by a tube 122 to CPAP air supply 121. This provides a secure and comfortable device for supplying CPAP air to the patient while avoiding many of the complications attendant with using conventional CPAP devices. Referring to FIGS. 14A and 14B, a shield 36 can be modified to fit over tubes 80 but otherwise function as described above.

Referring to FIG. 8, in yet another embodiment of the invention, a first securing mechanism such as clip 91 is connected through tether mechanism 92 to a second securing mechanism such as a looped strap with hook and loop portions 93 and 94. The first securing mechanism can be secured to an article of clothing worn by the user. The second securing mechanism can be secured to the apparatus, for example by passing part of the tether around shield 36a and connecting hook and loop portions 93 and 94 to for a loop of tether. This allows ready recovery of the apparatus in case it is accidentally removed from the user's mouth. This is particularly helpful in case the apparatus slips out at night while the user is sleepy and may not be aware of where the apparatus may have ended up. This is also helpful in many care-giving situations for the aged, paraplegic, handicapped or others with compromised manual dexterity. This or a similar tether can be used in combination with other tongue sleeve and shield combinations described above.

The apparatus has the following advantages:
1. The generic design of the apparatus can fit most user's without modification, thus reducing the cost to the user. The apparatus is so designed that is does not need the services of a professional for adaptation to an individual. It can be self-fitted by the user for maximum benefit.
2. The tongue compartment may be made in multiple sizes, e.g., medium, large and extra large, to better accommodate a variety of tongue sizes. Smaller sizes, such as those for use with pediatric and infant applications, can also be provided.
3. The tongue sleeve or tongue pouch is so designed as to allow better tongue control, by grasping and keeping it in a protrusive position determined by a labial shield.
4. The method for extending the tongue is controlled by notches along each side of the tongue compartment.
5. The overall size of the appliance is relatively small, thus more comfortable. It relieves psychological stress, allowing muscles to relax and enable better treatment of snoring.
6. The design of the tongue retention shield allows those who are mouth breathers to breathe normally, without need for bulky airways. It is also easy to breathe around the apparatus.
7. The appliance is designed in the posterior area to allow minimal vertical opening, which will avoid TMJ problems.
8. The thickness, in the posterior region, of the apparatus material is such that it will prevent damage caused by bruxism.

9. The appliance may be made in colors so that it may be identified easily. It may be designed to be opaque or generally translucent, which makes it more attractive to wear.

10. The apparatus is marked so that it cannot be inserted in the wrong manner, and with holes for breathing and reinforcement flanges to determine the correct position.

A general description of the apparatus and method of using the present invention as well as a preferred embodiment of the present invention has been set forth above. One skilled in the art will recognize and be able to practice many changes in many aspects of the apparatus and method described above, including variations which fall within the teachings of this invention. The spirit and scope of the invention should be limited only as set forth in the claims which follow.

What is claimed is:

1. In a tongue positioning apparatus, the combination comprising
    a) a tongue sleeve having a top surface, configured for reception and retention of the forward extent of the user's tongue, and configured to be retained by the user's mouth,
    b) an airway on the tongue sleeve having an outlet positioned on the top surface of the tongue sleeve and an inlet, wherein the inlet communicates from the exterior of the user's mouth to the outlet in the interior of the user's mouth when the apparatus is retained by the user's mouth,
    c) a removable shield means shaped to be received and retained outwardly of the user's lip having a shelf unitary with the shield means and extending at an angle from the shield which is configured to receive the user's lips, and
    d) an attachment means for attaching the shield means to said tongue sleeve to permit positioning the shield means and the shelf relative to the tongue forward extent whereby the tongue may be comfortably positioned and retained in said tongue sleeve, whereby snoring is reduced as the tongue is brought forward, out of the mouth, and forward movement of the shield means will move the tongue so as to provide lessened airway obstruction.

2. The tongue positioning apparatus of claim 1 wherein said airway comprises a tube secured to said tongue sleeve, said tube communicating with the interior of the user's mouth and outside the user's mouth when the apparatus is positioned for use.

3. The tongue positioning apparatus of claim 1 further comprising a plurality of airways.

4. The tongue positioning apparatus of claim 2 further comprising a plurality of said tubes.

5. The tongue positioning apparatus of claim 1 further comprising a vacuum fitting means connected to said tongue sleeve.

6. The tongue positioning apparatus of claim 5 wherein said vacuum fitting means comprises a valve.

7. The tongue positioning apparatus of claim 1 wherein said tongue sleeve further comprises flaring lobes, rearwardly crescent-shaped.

8. The tongue positioning apparatus of claim 1 further comprising between the anterior and posterior portion of said tongue sleeve,
    a vertical narrow portion in the superior-inferior dimension of said tongue sleeve,
    a horizontal narrow portion in the right-left dimension of said tongue sleeve,
    wherein said vertical and horizontal narrow portions form a constricted portion of the interior of said tongue sleeve.

9. The tongue positioning apparatus of claim 8 wherein said vertical and horizontal narrow portions form an annular constricted portion.

10. The tongue positioning apparatus of claim 1 wherein said attachment means comprises adjustable attachment means for adjustably attaching the shield means to said tongue sleeve to permit selective adjustment of the position of the shield means relative to the tongue forward extent.

11. The tongue positioning apparatus of claim 1 wherein said attachment means comprises notches which are presented sidewardly of said tongue sleeve.

12. The tongue positioning apparatus of claim 11 wherein said tongue sleeve has a forward portion and said notches are connected to said forward portion.

13. The tongue positioning apparatus of claim 12 wherein said walls flare rearwardly of said notches.

14. The tongue positioning apparatus of claim 11 wherein the tongue sleeve has flexible plastic walls, and is oval shaped in cross section laterally between said notches.

15. The tongue positioning apparatus of claim 11 wherein said shield means has an inner edge portion adjustably receivable in said notches.

16. The tongue positioning apparatus of claim 1 wherein said shield means is shaped to accommodate the airway.

17. The tongue positioning apparatus of claim 1 wherein the shield means comprises a flexible plastic sheet.

18. The tongue positioning apparatus of claim 1 wherein the shield means comprises a rigid plastic sheet.

19. The tongue positioning apparatus of claim 1 wherein the shield means further comprises a rigid plastic sheet with an opening positioned to align with the airway.

20. The tongue positioning apparatus of claim 1 wherein said angle is from approximately 70° to approximately 90°.

21. The tongue positioning apparatus of claim 1 wherein the shelf is configured to receive the user's lips and front teeth.

22. The tongue positioning apparatus of claim 21 further comprising an elastomeric material secured to said shelf.

23. The tongue positioning apparatus of claim 21 wherein the shield means further comprises a moldable material secured to said shelf, said moldable material conformed to fit the user's bite.

24. The tongue positioning apparatus of claim 21 wherein the shelf extends at an angle from said shield to receive a user's lips and dental arch.

25. The tongue positioning apparatus of claim 24 wherein the shelf further comprises an elastomeric material secured to said shelf.

26. The tongue positioning apparatus of claim 1 wherein the airway comprises an air channel formed in the tongue sleeve, the air channel communicating with the interior of the user's mouth and outside the user's mouth when the apparatus is retained by the user's mouth.

27. The tongue positioning apparatus of claim 26 further comprising a plurality of the air channels.

28. The tongue positioning apparatus of claim 10 wherein the adjustable attachment means is configured to bring the user's tongue forward from 1 to 4 centimeters.

29. The tongue positioning apparatus of claim 26 wherein said shield means lies along said tongue sleeve to further define said air channel.

30. The tongue positioning apparatus of claim 1 further comprising a tether, said tether comprising
- strap means having a first and a second end,
- a first securing means connected to said first end of said strap means, and
- a second securing means connected to said second end of said strap means.

31. The tongue positioning device of claim 2 wherein the tube is configured to connect to a positive airway pressure supplying means.

32. The tongue positioning apparatus of claim 31 wherein the tube is configured to mate with a nasal pillow of the positive airway pressure supplying means.

33. The tongue positioning apparatus of claim 24 wherein the shield means further comprises a moldable material secured to said shelf, said moldable material conformed to fit the user's bite.

* * * * *